(12) United States Patent
Nawrat et al.

(10) Patent No.: US 9,610,135 B2
(45) Date of Patent: Apr. 4, 2017

(54) LAPAROSCOPIC MEDICAL INSTRUMENT HOLDING DEVICE

(71) Applicant: FUNDACJA ROZWOJU KARDIOCHIRURGII IM. PROF. ZBIGNIEWA RELIGI, Zabrze (PL)

(72) Inventors: Zbigniew Nawrat, Zabrze (PL); Lukasz Mucha, Przemysl (PL); Krzysztof Lehrich, Ustron (PL); Krzysztof Lis, Wilkowice (PL)

(73) Assignee: FUNDACJA ROZWOJU KARDIOCHIRURGII IM. PROF. ZBIGNIEWA RELIGI, Zabrze (PL)

( * ) Notice: Subject to any disclaimer, the term of this patent is extended or adjusted under 35 U.S.C. 154(b) by 0 days.

(21) Appl. No.: 14/867,088

(22) Filed: Sep. 28, 2015

(65) Prior Publication Data

US 2016/0346060 A1 Dec. 1, 2016

(30) Foreign Application Priority Data

May 29, 2015 (EP) .................................... 15169890

(51) Int. Cl.
*A61B 90/50* (2016.01)
*F16B 2/06* (2006.01)
(Continued)

(52) U.S. Cl.
CPC ............ *A61B 90/50* (2016.02); *A61B 1/0016* (2013.01); *A61B 1/00149* (2013.01);
(Continued)

(58) Field of Classification Search
CPC ............ A61B 1/00133; A61B 1/00147; A61B 1/00149; A61B 1/0016; A61B 8/4029;
(Continued)

(56) References Cited

U.S. PATENT DOCUMENTS

| 1,691,155 A | * | 11/1928 | Howell | ................... B60R 11/00 |
| | | | | 248/316.5 |
| 5,577,697 A | * | 11/1996 | Accordino | ............. F16M 13/02 |
| | | | | 248/206.5 |

(Continued)

FOREIGN PATENT DOCUMENTS

| WO | WO 2004/039250 A1 | 5/2004 | ................ A61B 1/00 |
| WO | WO 2008/142672 A1 | 11/2008 | ................ A61B 1/00 |
| WO | WO 2013/156024 A1 | 10/2013 | ................ A61B 1/04 |

OTHER PUBLICATIONS

Extended European Search Report mailed Dec. 10, 2015 in corresponding application No. 15169890.9.

*Primary Examiner* — Jonathan Liu
*Assistant Examiner* — Guang H Guan
(74) *Attorney, Agent, or Firm* — Renner Kenner Greive Bobak Taylor & Weber

(57) ABSTRACT

The laparoscopic medical instrument holding device has a platform with a holder for securing the instrument. The holder has at least two clamping claws arranged on the platform and each of the clamping claws comprises a two-arm base. Each arm of the base has movably mounted thereon a claw and each arm of the claw has at least two guide rollers. The arm of the claw has a ferromagnetic material footing located above a magnet mounted on the platform. A holding force between the footing and the magnet is adjustable. In the holder there is a releasably mounted instrument sleeve for securing the laparoscopic instrument. The instrument sleeve has a pair of internally mounted clamping elements and an externally mounted securing nut coupled via a deflecting transmission to a motor unit attached to the platform.

10 Claims, 9 Drawing Sheets

(51) Int. Cl.
*F16M 13/02* (2006.01)
*A61B 1/00* (2006.01)
*A61B 1/313* (2006.01)
*A61B 34/30* (2016.01)
*F16B 1/00* (2006.01)

(52) U.S. Cl.
CPC ............. *A61B 1/3132* (2013.01); *F16B 2/06* (2013.01); *F16M 13/022* (2013.01); *A61B 2034/301* (2016.02); *A61B 2034/302* (2016.02); *F16B 2001/0035* (2013.01)

(58) Field of Classification Search
CPC . A61B 90/50; A61B 90/57; F16B 2/06; F16B 2/10; F16B 2/16
USPC .......... 600/102, 106; 606/1, 130; 248/316.1, 248/316.2, 316.3, 316.5, 346.01, 346.03, 248/346.04, 67.5, 67.7, 73, 230.4, 231.21, 248/231.51, 206.5, 122.1; 269/3, 6, 95
See application file for complete search history.

(56) References Cited

U.S. PATENT DOCUMENTS

| | | | | |
|---|---|---|---|---|
| 5,590,567 A * | 1/1997 | Marrs | ...................... | F16C 1/105 248/67.7 |
| 5,730,622 A * | 3/1998 | Olson | ...................... | H01R 24/44 439/575 |
| 5,871,448 A * | 2/1999 | Ellard | .................. | A61B 8/0841 600/459 |
| 6,451,027 B1 | 9/2002 | Cooper et al. | ................ | 606/130 |
| 6,659,956 B2 * | 12/2003 | Barzell | ...................... | A61B 8/12 600/461 |
| 6,821,243 B2 * | 11/2004 | Pagliuca | ................ | A61B 90/50 600/102 |
| 6,932,760 B1 | 8/2005 | Pang et al. | ..................... | 600/112 |
| 7,309,311 B2 * | 12/2007 | Otsuka | ............... | A61B 1/00149 600/102 |
| 7,492,116 B2 * | 2/2009 | Oleynikov | ............. | A61B 1/041 318/568.11 |
| 7,699,855 B2 * | 4/2010 | Anderson | .............. | A61B 34/71 606/1 |
| 8,246,551 B2 * | 8/2012 | Miller | ................ | A61B 10/0275 600/564 |
| 8,720,841 B2 * | 5/2014 | Morren | ..................... | F16B 2/10 248/229.2 |
| 8,783,636 B2 * | 7/2014 | Okita | ................... | F16M 11/041 24/303 |
| 8,814,118 B2 * | 8/2014 | Okita | .................... | H01F 7/0252 24/495 |
| 9,066,746 B2 * | 6/2015 | Mirza | ............ | A61B 17/320036 |
| 9,089,356 B2 * | 7/2015 | Chen | ..................... | A61B 10/06 |
| 9,211,160 B2 * | 12/2015 | Pivotto | ................ | A61B 19/2203 |
| 9,237,930 B2 * | 1/2016 | Hauck | .................. | A61B 1/0052 |
| 2003/0076410 A1 | 4/2003 | Beutter et al. | ................. | 348/65 |
| 2004/0143188 A1 * | 7/2004 | Barzell | ..................... | A61B 8/12 600/439 |
| 2004/0267089 A1 | 12/2004 | Otsuka et al. | ................ | 600/102 |
| 2005/0162383 A1 | 7/2005 | Rosenberg | .................... | 345/156 |
| 2008/0091066 A1 | 4/2008 | Sholev | ........... | 600/112 |
| 2010/0185212 A1 | 7/2010 | Sholev | ........... | 606/130 |
| 2012/0029277 A1 | 2/2012 | Sholev | ........... | 600/102 |
| 2012/0130159 A1 | 5/2012 | Abri et al. | ............ | 600/102 |
| 2012/0172850 A1 | 7/2012 | Kappel et al. | ..................... | 606/1 |
| 2012/0302890 A1 * | 11/2012 | Strong | ................ | A61N 5/1027 600/459 |
| 2013/0150669 A1 | 6/2013 | Deng et al. | ................. | 600/109 |
| 2014/0221738 A1 | 8/2014 | Sholev et al. | ............... | 600/102 |
| 2015/0141914 A1 * | 5/2015 | Fasano | ............ | A61M 25/0113 604/95.01 |
| 2015/0320392 A1 * | 11/2015 | Missov | ................. | A61B 90/50 600/466 |
| 2016/0346060 A1 * | 12/2016 | Nawrat | ................. | A61B 90/50 |

* cited by examiner

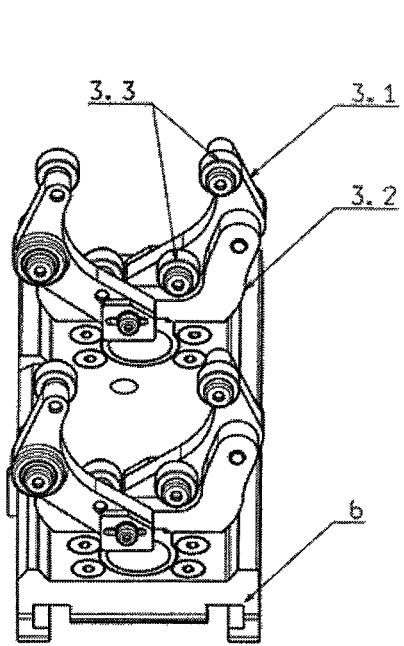
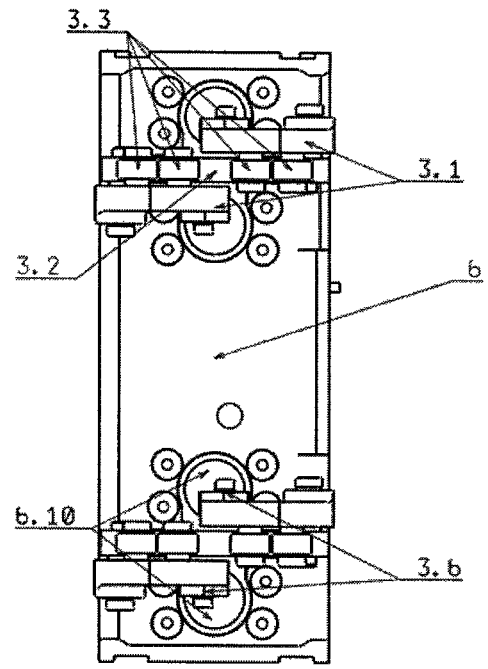
Fig. 8          Fig. 9
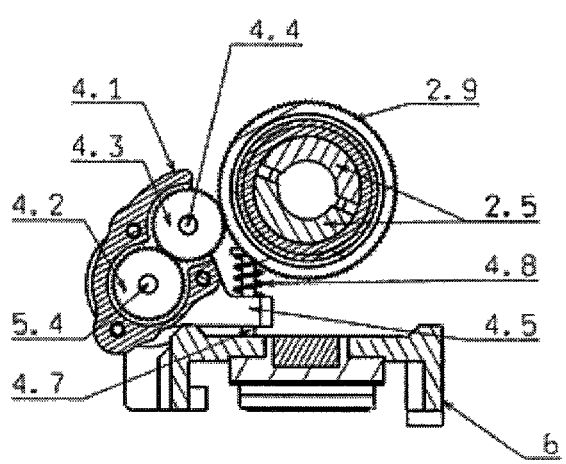
Fig. 10

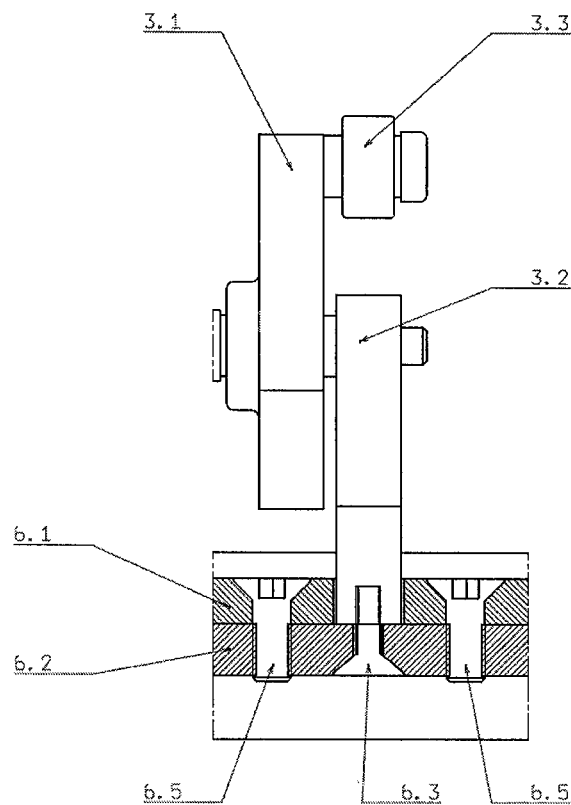
Fig. 17
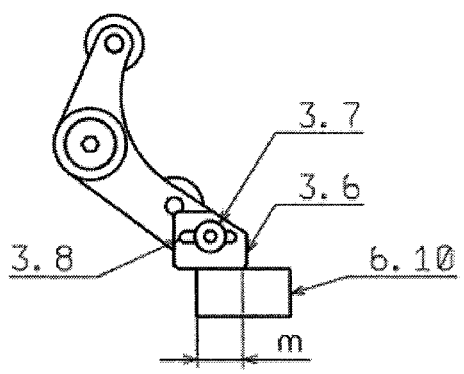 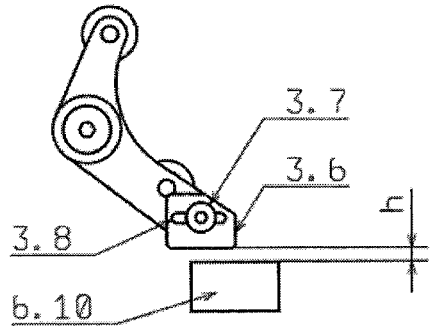
Fig. 18                Fig. 19

LAPAROSCOPIC MEDICAL INSTRUMENT HOLDING DEVICE

TECHNICAL FIELD

The present invention relates to a laparoscopic medical instrument holding device, used for supporting surgeries and surgical procedures, in particular for securing laparoscopic instruments in assemblies in which surgical robots are used.

BACKGROUND ART

A holder for attaching a laparoscopic instrument releasably, in particular an endoscopic camera is known from US 2004/0267089 A1. This holder is coupled to endoscopic cameras having two pairs of fixing pins on the outside circumference of the housing. The holder comprises a fixing arm mounted on one side on a base for stable supporting the holder on a surface, to the other side of which arm is mounted a grip for securing the endoscopic camera. The grip comprises a body having a pair of L-shaped claws, wherein the body in the rear part is connected to the arm, whereas the front part thereof is used for securing the endoscopic camera. A first L-shaped claw is immovably fixed in the lower part of the body, from the side used for securing the endoscopic camera. The arms of the first claw are separated by a distance equal to the width of the housing of the endoscopic camera. At the same time the arms of the first claw are mounted in such a manner that the shorter ends thereof are directed upwards. In the upper part of the body, parallel to the first claw there is a movably mounted second L-shaped claw whose shorter ends of the arms are directed downwards, whereas the longer ends of the arms protrude beyond the rear part of the body. The movable connection is achieved by means of an axis in the body and going through the longer ends of the arms. In the rear part of the longer ends of the arms, behind the body, there is a through hole in which there is a mandrel supported by a spring, wherein said mandrel also goes through the element connecting the body to the fixing arm. The upper part of said mandrel ends with a flange which does not go through the hole in the longer end of the arm, wherein between the flange and the surface of the arm there is an expanding spring. The endoscopic camera is secured in the body in such a manner that the first pair of fixing pins is arranged in the first immovable claw, and by pressing the flange of the mandrel the upper claw is opened, the endoscopic camera is appropriately arranged after which the pressure is released, thus clamping the claw on the second pair of fixing pins of the endoscopic camera.

US2012/0029277 discloses a method for controlling an endoscope during laparoscopic surgeries. The method for controlling the endoscope consists in using a pivoting support coupled to an endoscopic camera, wherein said support comprises a mechanism enabling the coupled endoscopic camera to move independently, for example, in two arc-shaped paths. Therefore the mechanism coupled to the endoscopic camera enables movement in four degrees of freedom. At the same time the pivoting support including the mechanism is connected to an adjustable arm mounted on a base which can be attached to an operating table. By using said adjustable arm it is possible to control the position of the endoscopic camera with the control mechanism thereof in the operating field.

For example, US 2003/0076410 A1 discloses powered zoom couplers being a part of endoscopic viewing systems including cameras. Said coupler is mounted between a proximal end of an endoscope and the camera with a transducer producing an output signal transmitted to a monitor displaying the image. Said coupler includes a sleeve inside which there is a plurality of lenses for optically enhancing the image received from the endoscope. Owing to the properties of the lenses the image can be, for instance, magnified. Said lenses inside the sleeve are mounted movably, the position of said lenses in relation to one another and in relation to the ends of the sleeve is set with the use of two motor units coupled to selected groups of optical elements. Therefore, the image generated by the endoscope before the camera head is modified by a plurality of lenses. Moreover, the viewing system also comprises a sensor mounted inside the sleeve, said sensor indicating the current position of the lenses. Said sensor is coupled to a processor controlling the motor units and receiving commands generated from outside.

SUMMARY OF THE INVENTION

The object of the invention is to provide a laparoscopic medical instrument holding device with a simple structure and enabling stable holding of various laparoscopic medical instruments with laparoscopic cannulas of different diameter without the need to adapt either the holding device or the laparoscopic instrument housing. It is also the object of the invention to provide a structure which can be utilized with surgical robots and protected against mechanical damage. Still another object of the invention is to provide a secure attachment of a laparoscopic instrument without causing damage of the instrument in place of connection to the holder. Another object of the invention is to enable sterilization of the instrument without the need to disassemble many elements of the holding device while also enabling pivoting movement of the instrument around its axis after securing said instrument in the holding device.

This invention relates to a laparoscopic medical instrument holding device. The essence of the invention consists in that the holder has a form of at least two clamping claws arranged on a platform at a distance from each other, wherein each of the clamping claws comprises a two-arm base. An arm of the claw is attached movably to each arm of said base, and each arm of the claw includes at least two guide rollers mounted on opposite sides of the movable connection of the arm of the claw with the arm of the base and also includes a footing with a ferromagnetic element. The footing of the arm of the claw is positioned above a magnet mounted on the platform. At the same time in order to adjust the holding force between the footing and the magnet, the footing is mounted slidably on the arm of the claw while maintaining a constant distance from the magnet, and said magnet is mounted slidably on the platform with the possibility to adjust the distance between said magnet and the footing. Moreover, there is an instrument sleeve mounted releasably in the holder for securing the medical instrument including therein a pair of clamping elements and a securing nut mounted outside coupled via a deflecting transmission to a motor unit attached to the platform, wherein on the outside circumference of the instrument sleeve or on the outside circumference of the securing nut there is at least one groove for the guide rollers.

It is advisable that the magnets for one clamping claw be mounted on a common base connected to the platform with screws.

It is also recommendable that each arm of the claw be rotatably attached to the arm of the base with the use of a bearing.

In one embodiment a mount may be attached to the platform, said mount having an inside hole with a circular cross section, inside said hole there be rotatably mounted two flanged sleeves inside which there be a stator of the motor unit.

In another embodiment there is a deflecting transmission immovably mounted to the stator of the motor unit, said deflecting transmission having a partially open body inside which there is a driving wheel mounted on the motor unit shaft and a driven wheel rotatably mounted on the axis mounted in the body.

In still another embodiment the body from the side of the instrument sleeve may have a spline with a through hole with a screw therein, said screw being screwed into the platform and pressed down with a spring.

In one embodiment the instrument sleeve on the outside surface thereof may have a thread and the inside hole of the instrument sleeve on the opposite end is cone-shaped in the longitudinal cross-section through the axis, and the ends of the clamping elements have cone-shaped ends with tapering corresponding to the cone-shaped end of the instrument sleeve.

In another embodiment the groove on the securing nut and the groove on the outside circumference of the instrument sleeve may be cone-shaped in a cross section, said cone having positively matched thereto rolling surfaces of the guide rollers.

The securing nut may be coupled to the deflecting transmission with a toothed rim on the outside circumference of the securing nut.

In still another embodiment the securing nut may be coupled to the deflecting transmission with a friction surface on the outside circumference of the securing nut.

The main advantage of the invention is the possibility to mount laparoscopic instruments in the holding device, in particular endoscopic cameras with laparoscopic cannulas of different diameter without the need to adapt either the holding device or the laparoscopic instrument, which ensures that the holding device can be used for many different purposes while being easily set and the clamping force with which the instrument is held in the holding device can be adjusted. Adjusting the holding force substantially facilitates the use of the holding device in many medical procedures and also increases the security of using the holding device with medical robots. The increase in the security is a result of automatic release of the medical instrument from the holding device when the preset holding force is exceeded, for example, when the laparoscopic instrument guided by the surgical robot's arm meets an obstacle as a result of which the holding force is exceeded and the laparoscopic instrument is released from the holding device not leading to any damage of the patient's internal organs or the instrument itself. Another advantage is safe and stable securing of any laparoscopic instrument while maintaining undamaged surface of the instrument in the place where it meets the holder, which results not only in the versatility of the device, but also extends the life of the medical instruments mounted therein. Another advantage is the possibility to sterilize the holding device many times without the need to disassemble the elements thereof, thereby extending the life of the holding device and limiting the number of actions related to operating the holding device. Still another advantage is the possibility to perform a pivoting movement of the laparoscopic instrument mounted in the holding device, in particular an endoscopic camera, which enables a simple change of the viewing field of the camera in the event of using angular cameras.

BRIEF DESCRIPTION OF THE DRAWINGS

The invention is presented in more detail in embodiments and in a drawing, where FIG. 8 is the holding device in a perspective view of the clamping claws, FIG. 9 is the holding device in a top view of the clamping claws, FIG. 10 is a cross section of the holding device, FIG. 17 is a longitudinal cross section through a part of the platform of the holding device, FIG. 18 is a front view of the clamping claw arranged with a magnet, FIG. 19 is a front view of the clamping claw with the magnet in a different arrangement.

BEST MODE FOR CARRYING OUT THE INVENTION

Figure 1:
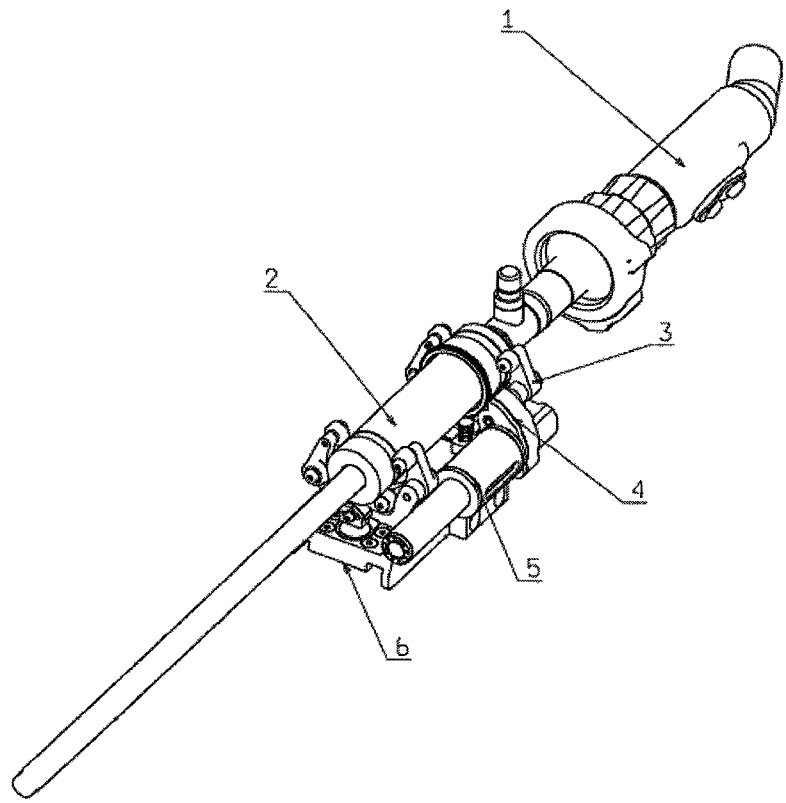
FIG. 1 is a perspective view of a device holding a laparoscopic medical instrument with an endoscopic camera mounted therein.
Figure 2:
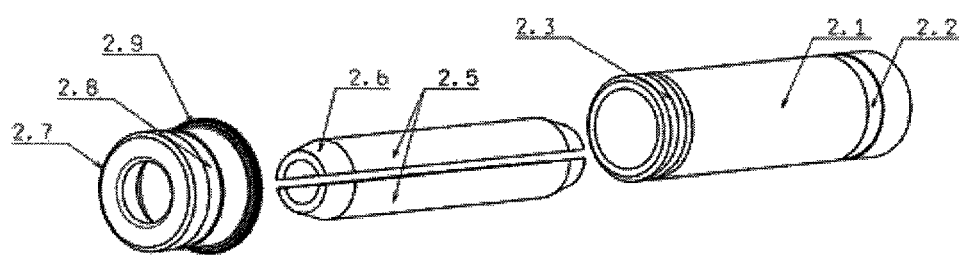
FIG. 2 is an exploded perspective view of an instrument sleeve.
Figure 3:
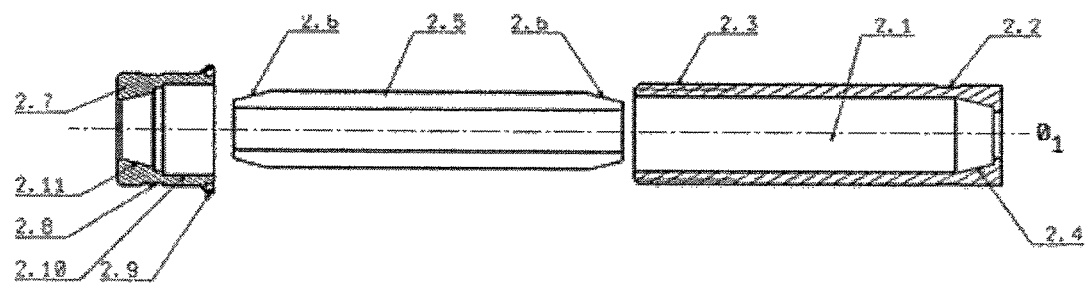
FIG. 3 is a cross section through the longitudinal axis in a exploded view of the instrument sleeve.
Figures 4, 5:
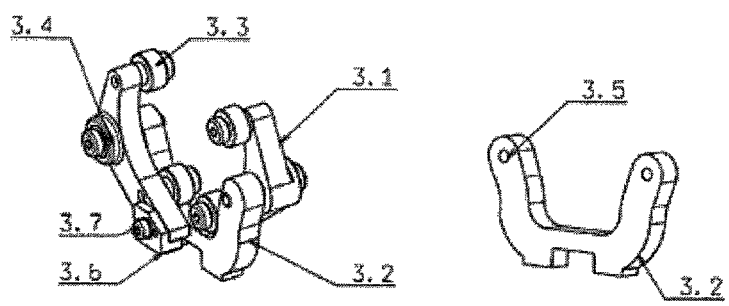
FIG. 4 is a perspective view of a holder.
FIG. 5 is a perspective view of a two-arm base for securing clamping claws.
Figures 6, 7:
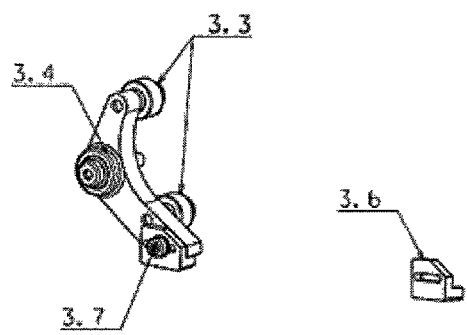
FIG. 6 is a perspective view of the clamping claw.
FIG. 7 is a perspective view of a footing made from ferromagnetic material mounted on the clamping claw.
Figure 11:
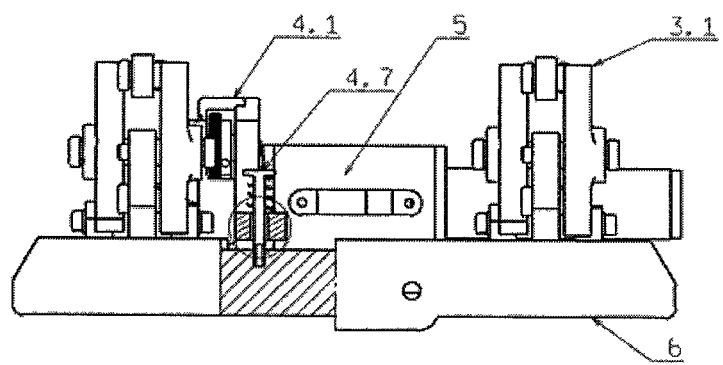
FIG. 11 is a side view of the holding device.
Figures 12, 13:
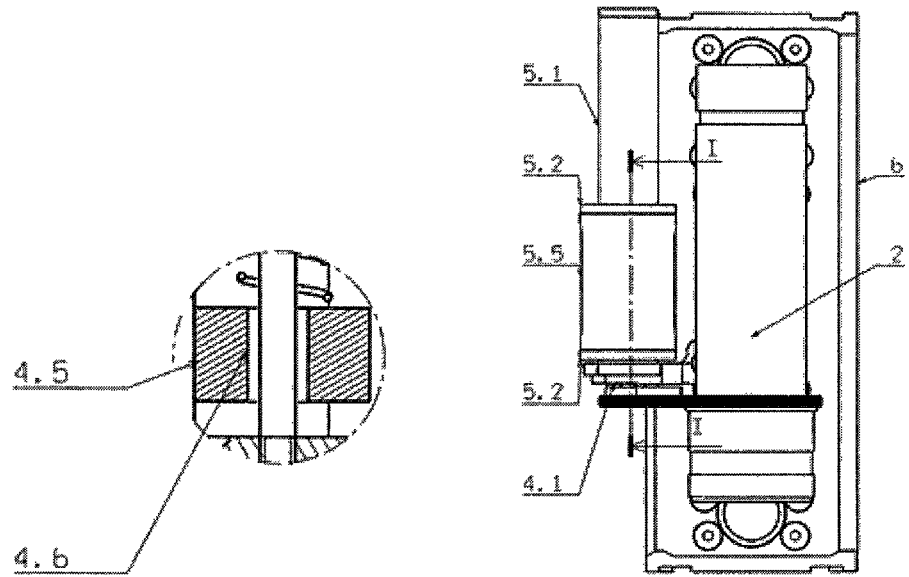
FIG. 12 is a detailed side view of a spline of the body of the deflecting transmission of FIG. 11.
FIG. 13 is the holding device in a top view of the instrument sleeve with a motor unit.
Figure 14:
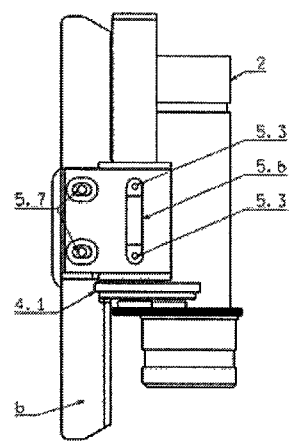
FIG. 14 is a side view of the motor unit.
Figure 15:
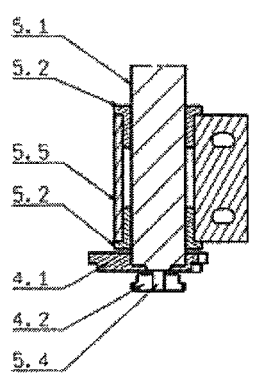
FIG. 15 is a cross section through the longitudinal axis of the motor unit.
Figure 16:
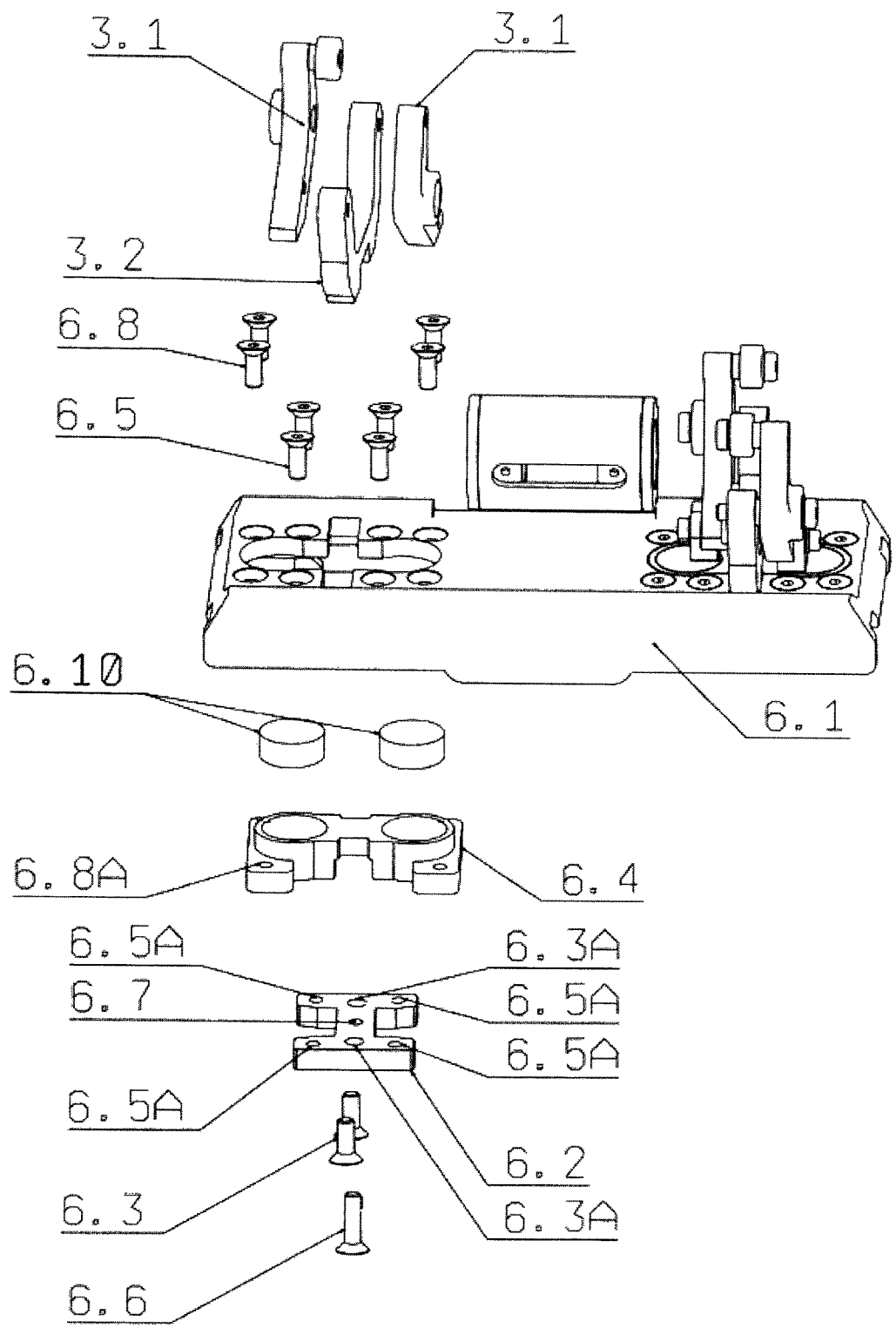
FIG. 16 is a partly exploded perspective view of the holding device.
Figure 20:
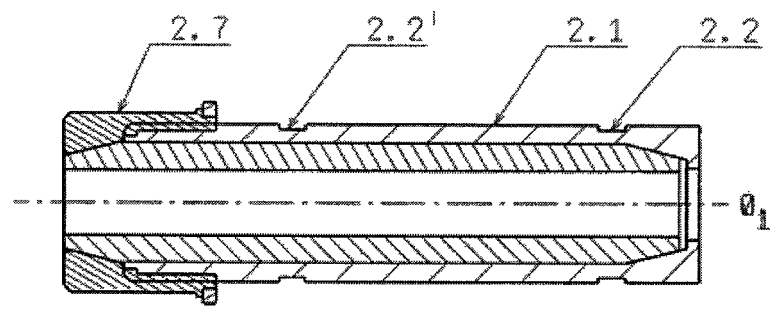
FIG. 20 is a cross section through the longitudinal axis of the instrument sleeve in a different embodiment.
Figure 21:
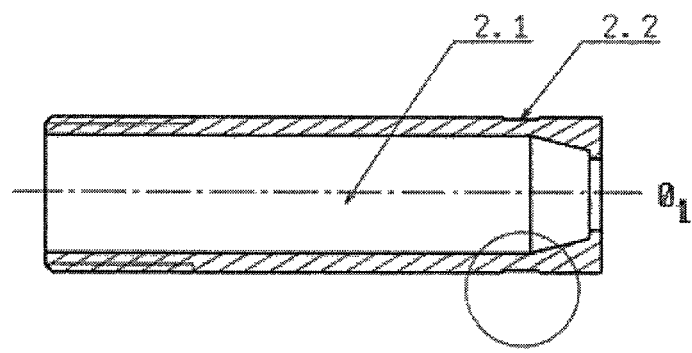
FIG. 21 is a cross section through the longitudinal axis of the instrument sleeve in another embodiment.
Figure 22:
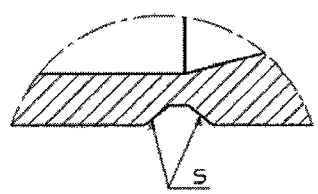
FIG. 22 is a detail from FIG. 21, namely the groove.
Figure 23:
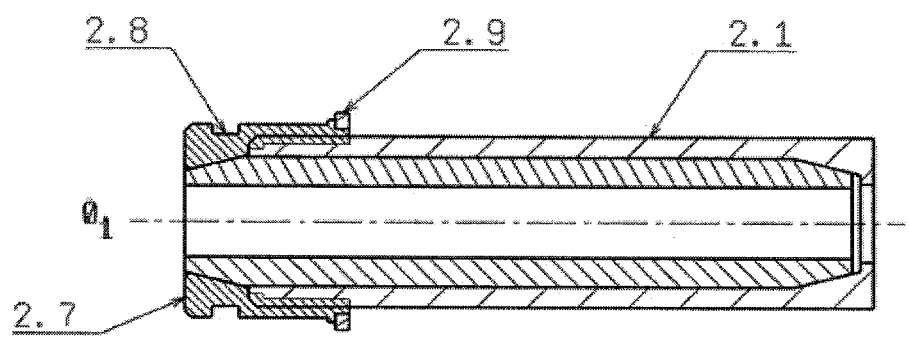
FIG. 23 is a cross section through the longitudinal axis of the instrument sleeve in another embodiment.

A laparoscopic medical instrument 1 holding device has a platform 6 and on the platform 6 there is a holder 3 for releasable mounting of an instrument sleeve 2, inside which there is a directly mounted medical instrument 1. There is also a motor unit 5 directly connected to the platform 6 and the motor unit is coupled through a deflecting transmission 4 to the instrument sleeve 2.

The holder 3 has a pair of clamping claws mounted on the platform 6. The clamping claws which form the holder 3 are arranged along the length of the platform 6 at such a distance from each other that it is possible to secure therein the instrument sleeve 2 in a stable manner. Each clamping claw is mounted on the platform 6 by means of a two-arm base 3.2, and the two-arm base 3.2 is secured between two permanent magnets 6.10 mounted on the platform 6.

Each two-arm base 3.2 is screwed to an auxiliary base 6.2 with screws 6.3 at points 6.3A. The auxiliary base 6.2 is immovably screwed to a body 6.1 of the platform 6 with screws 6.5 at points 6.5A.

The permanent magnets 6.10 are carried by the platform 6 by a common base 6.4 located between the body 6.1 of the platform 6 and the auxiliary base 6.2. The common base 6.4 that carries the magnets 6.10 is attached between the body 6.1 and the auxiliary base 6.2 by means of a screw 6.6 going through a hole 6.7 and screwed to the common base 6.4 with the magnets 6.10. From the top of the common base 6.4 with the magnets 6.10 is screwed with screws 6.8 going through holes in the body 6.1 of the platform 6 and screwed into threaded holes 6.8A.

By connecting the magnets 6.10 to the platform 6 with the screws 6.6, 6.8 it is possible to adjust the distance h of the magnets 6.10 from the auxiliary base 6.2. In order to change the position of the magnets 6.10 one should unscrew the screws 6.8 connecting the common base 6.4 of the magnets 6.10 with the body 6.1 and then by screwing or unscrewing the screw 6.6 it is possible to change the distance h of the common base 6.4 of the magnets 6.10 in relation to the auxiliary base 6.2. In order to lower the base 6.4, after unscrewing the screws 6.8, one should screw the screw 6.6 into the common base 6.4 of the magnets 6.10 and then tighten the screws 6.8. In order to raise the common base 6.4 and reduce the distance h of the magnets 6.10 from the auxiliary base 6.2 one should unscrew the screws 6.6 and tighten the screws 6.8.

In another embodiment the two-arm base 3.2 can be mounted above one permanent magnet with the length exceeding the width of the base 3.2, mounted directly on the platform 6 or on the common base 6.4 adapted for a single magnet.

To each arm of the base 3.2 at a point 3.5 there is rotatably mounted, with the use of a bearing 3.4 an arm of a claw 3.1. As a result both arms of the claw 3.1 are mounted in an angular deflecting manner. Each arm of the claw 3.1 has two guide rollers 3.3 arranged at the opposite sides of the point 3.5 of the connection with the arm of the base 3.2. In the part of the arm of the claw 3.1 which is closer to the platform 6 there is mounted a footing 3.6 comprising a ferromagnetic element. In other words, the footing includes a ferromagnetic insert or is entirely made from ferromagnetic material. The footing 3.6 is above the permanent magnet 6.10 mounted on the platform 6. The footing 3.6 is screwed down to the arm of the claw 3.1 with a screw 3.7 going through a guide groove 3.8 made in the footing 3.6, which enables moving the footing 3.6 while maintaining a constant distance from the magnet 6.10 in the set position thereof.

The magnetic field created between the permanent magnets 6.10 and the footings 3.6 of each clamping claw leads to drawing of the footing 3.6 to the magnet 6.10 and maintaining the arms of the claw 3.1 in a set position, which also means clamping them on the instrument sleeve 2 in which the laparoscopic instrument 1 is secured.

The laparoscopic instrument 1 is placed within the body 2.1 of the instrument sleeve 2 between two clamping elements 2.5 located therein whose ends are cones 2.6. The interior of the body 2.1 of the instrument sleeve 2 in the longitudinal cross section through the axis $O_1$ thereof has a form of a cone 2.4 at one end with the same tapering angle as the conical ends 2.6 of the clamping elements 2.5. The opposite end of the body 2.1 of the instrument sleeve 2 on the outside circumference thereof has a thread 2.3 coupled to a thread 2.10 of a securing nut 2.7 wound on the instrument sleeve 2. Moreover, on the outside circumferences of the instrument sleeve 2 and the securing nut 2.7 there are grooves 2.2, 2.8 for the guide rollers 3.3 of the arms of the claws 3.1, wherein on the outside circumference of the securing nut 2.7 there is also a toothed rim 2.9 coupled by means of a deflecting transmission 4 to a motor unit 5. The internal surface of the securing nut 2.7 has the shape of a cone 2.11 with the tapering angle corresponding with the conical ends 2.6 of the clamping elements. After securing the laparoscopic instrument 1 inside the body 2.1 of the instrument sleeve 2 the securing nut 2.7 is tightened, which results in moving of the clamping elements 2.5 to the end of the instrument sleeve 2 and that leads to uniform clamping of the laparoscopic instrument 1 along the length thereof, and therefore both sliding and rotation of the instrument in relation to the instrument sleeve 2 is blocked. The whole instrument sleeve 2 may be sterilised after assembly.

In another embodiment on the outside circumference of the instrument sleeve 2 there can be two guide grooves 2.2, 2.2'.

In a preferred embodiment the guide grooves 2.2, 2.8 on the instrument sleeve 2 and on the securing nut 2.7 have conical side surfaces to which there are positively fitted rolling surfaces of the guide rollers 3.3.

In yet another embodiment there can be only one guide groove 2.8 on the outside circumference of the securing nut 2.7. The instrument sleeve 2 remains smooth in this embodiment and the guide rollers 3.3 lean directly on the outside surface of the instrument sleeve 2.

The motor unit 5 coupled to the securing nut 2.7 is secured in a mount 5.5 with a circular internal cross section screwed down to the platform 6 with screws 5.7. The motor unit 5 comprises a motor with a stator 5.1 mounted in two flanged sleeves 5.2, wherein the possibility to move of the stator 5.1 in relation to the sleeve 5.2 is blocked by means of flat head machine screws 5.3. The sleeves 5.2 are so arranged that it is possible to rotate the shaft 5.4 of the motor unit 5, wherein said sleeves 5.2 are so rotatably mounted in the mount 5.5 that the flanges of the sleeve 5.2 lean against the walls of the mount 5.5 thus making it impossible for the motor to slide along the axis thereof, but enabling the stator 5.1 to rotate around the axis of the mount 5.5. Moreover, access to the screws 5.3 through a recess 5.6 is possible, which enables their assembly and disassembly.

Coupling the motor unit 5 to the securing nut 2.7 is achieved by the deflecting transmission 4 which has a deflecting body 4.1 partly open from the side of the instrument sleeve 2 and the deflecting body 4.1 is immovably mounted to the stator 5.1 of the motor unit 5. Inside the body 4.1 there is a driving wheel 4.2 immovably mounted on the shaft 5.4 of the motor unit 5 and a toothed driven wheel 4.3 rotatably mounted on the axis 4.4 in the body 4.1, wherein the driven wheel 4.3 partly protrudes beyond the body 4.1. The partly open body 4.1 enables engagement of the driven wheel 4.3 with the toothed rim 2.9 on the securing nut 2.7. From the side of the instrument sleeve 2 the body 4.1 has a spline 4.5 with a hole 4.6. Through the hole 4.6 goes a screw 4.7 screwed to the platform 6. The screw 4.7 in the upper part thereof is wound with a spring 4.8 pressing down the body 4.1 with the internal mechanisms to the toothed wheel 2.9. The screw 4.7 also adjusts the pressing force of the deflecting transmission 4 on the instrument sleeve 2.

In another embodiment on the outside circumference of the securing nut 2.7 there may be a friction surface provided for coupling with appropriately adapted elements of the deflecting transmission 4.

Assembly of the instrument sleeve 2 with the mounted therein laparoscopic instrument 1 on the platform 6 consists in arranging the instrument sleeve 1 in such a manner that the guide rollers 3.3 on the angular deflecting arms 3.1 of the clamping claws correspond with the guide groove 2.2 of the instrument sleeve 2 and the guide groove 2.8 of the securing nut 2.7. After setting the required position the instrument sleeve 2 is pressed down towards the platform 6, which results in angular deflection of the arms 3.1 at the rotation point 3.5 and rotation of the motor unit 5 with the deflecting transmission 4 around the axis of the shaft 5.4 of the motor unit 5. By entering the guide grooves 2.2, 2.8, the guide rollers 3.3 block the possibility of the instrument sleeve 2 moving in relation to the longitudinal axis $O_1$. The magnetic field created between the permanent magnets 6.10 and the ferromagnetic footings 3.6 causes attraction of the footings 3.6 to the magnets 6.10 and clamping the arms 3.1 of the clamping claws on the instrument sleeve 2. At the same time the deflecting transmission 4 is pressed down by means of the spring 4.8 located between the head of the screw 4.7 and the spline 4.5. By adjusting the force of the screw 4.7 applied to the platform 6 the force of the deflecting transmission 4 pressing against the instrument sleeve 2 is adjusted. After actuating the motor unit 5 the rotational movement of the shaft 5.4 results in rotation of the mounted drive wheel 4.2 which transmits the rotational movement onto the driven wheel 4.3 and further to the toothed rim 2.9 of the securing nut 2.7, which results in rotational movement of the instrument sleeve 1.

The slidable adjustment of the position of the footing 3.6 while maintaining the constant distance between the footing 3.6 and the magnet 6.10 and the slidable adjustment of the position of the magnets 6.10 in relation to the auxiliary base 6.2 and thus the slidable adjustment of the distance between the magnets 6.10 and the ferromagnetic footing 3.6 enables the adjustment of the holding force of the instrument sleeve 2. The force needed for securing the instrument sleeve 2 in the holder 3 and the opposite force needed for withdrawing the instrument sleeve 2 from the holder 3 is set by changing the contact surface m of the footing 3.6 and the magnet 6.10. As indicated, changing the contact surface is achieved by unscrewing the screw 3.7 and moving the footing 3.6 along the groove 3.8 and by changing the distance h between the common base 6.4 of the magnets 6.10 and the auxiliary base 6.2, which results in the change of the distance between the footing 3.6 and the magnets 6.10 and the change of the force created between the footing 3.6 and the magnets 6.10.

Suitable adjustment of the holding force of the instrument sleeve 2 enables protecting the laparoscopic instrument 1 and, for example, tissues affected by the laparoscopic instrument from mechanical damage. When the force influencing the laparoscopic instrument exceeds the set values the footing 3.6 is uncoupled from the magnet 6.10 and the claws 3.1 open, which results in releasing the instrument sleeve 2 from the holders thus protecting the entire assembly from damage.

The invention claimed is:

1. A laparoscopic medical instrument holding device, comprising:
   a platform and at least two clamping claws for securing a laparoscopic medical instrument, wherein the at least two clamping claws are arranged on the platform at a distance from each other, and each of said at least two clamping claws comprises a base having two base arms, wherein a holding arm is movably attached at a connection to each of the two base arms of the base of each of said at least two clamping claws, each of the at least two clamping claws comprises at least two guide rollers attached to each holding arm and placed at opposite sides of the connection, each of the at least two clamping claws comprises a footing having a ferromagnetic element,
   wherein each footing of each of the at least two clamping claws is located above a corresponding magnet mounted in the platform,
   wherein in order to adjust a holding force between each footing of each of the at least two clamping claws and the corresponding magnet, each footing is slidably mounted to the corresponding holding arm of each of the at least two clamping claws while maintaining a distance from the corresponding magnet,
   wherein the corresponding magnet is slidably mounted in the platform such that the distance between each footing of each of the at least two clamping claws and the corresponding magnet is configured to be adjusted,
   wherein the laparoscopic medical instrument holding device further comprises an instrument sleeve releasably held by the at least two clamping claws and configured to secure the laparoscopic medical instrument and said instrument sleeve has a pair of clamping elements therein and a securing nut coupled via a deflecting transmission to a motor unit attached to the platform,
   wherein an outside circumference of the instrument sleeve or an outside circumference of the securing nut includes at least one groove for the guide rollers of one of the at least two clamping claws.

2. The laparoscopic medical instrument holding device according to claim 1, wherein the corresponding magnet for each footing of one of the at least two clamping claws is mounted on a common base, wherein the common base is connected to the platform with screws.

3. The laparoscopic medical instrument holding device according to claim 1, wherein each holding arm of each of the at least two clamping claws is rotatably mounted to the corresponding base arm of the two base arms of the base of the at least two clamping claws with a bearing.

4. The laparoscopic medical instrument holding device according to claim 1, wherein a mount is attached to the platform, wherein the mount has an internal hole with a circular cross section, and wherein two flanged sleeves are rotatably mounted inside the internal hole of the mount, and a stator for the motor unit is mounted inside the two flanged sleeves.

5. The laparoscopic medical instrument holding device according to claim 4, wherein the deflecting transmission is immovably mounted to the stator of the motor unit, the deflecting transmission has a partly open body, a drive wheel is mounted inside the partly open body of the deflecting transmission on a shaft of the motor unit, and a driven wheel rotatably mounted on an axis mounted in the partly open body of the deflecting transmission.

6. The laparoscopic medical instrument holding device according to claim 5, wherein the partly open body of the deflecting transmission has a spline at a side adjacent to the instrument sleeve, the spline has a through hole, a screw is screwed inside the through hole of the spline and into the platform, and the spline is pressed down by a spring.

7. The laparoscopic medical instrument holding device according to claim 1, wherein the instrument sleeve has an outside surface with threads, the instrument sleeve has an inside hole with a longitudinal end, the longitudinal end has a shape of a cone, the pair of clamping elements define cone-shaped ends each with a taper corresponding to the shape of the longitudinal end of the instrument sleeve.

8. The laparoscopic medical instrument holding device according to claim 1, wherein the at least one groove on either the outside circumference of the securing nut or the outside circumference of the instrument sleeve has conical side surfaces which receive the guide rollers of one of the at least two clamping claws.

9. The laparoscopic medical instrument holding device according to claim 8, wherein the securing nut is coupled to the deflecting transmission with a toothed rim made on the outside circumference of the securing nut.

10. The laparoscopic medical instrument holding device according to claim 8, wherein the securing nut is coupled to the deflecting transmission with a friction surface on the outside circumference of the securing nut.

* * * * *